(12) United States Patent (10) Patent No.: US 7,763,745 B2
Van Der Heide et al. (45) Date of Patent: **\*Jul. 27, 2010**

(54) PROCESS FOR THE PRODUCTION OF DIALKYL CARBONATE AND ALKANEDIOL

(75) Inventors: Evert Van Der Heide, Amsterdam (NL); Timothy Michael Nisbet, Amsterdam (NL); Garo Garbis Vaporciyan, Houston, TX (US)

(73) Assignee: Shell Oil Company, Houston, TX (US)

( * ) Notice: Subject to any disclaimer, the term of this patent is extended or adjusted under 35 U.S.C. 154(b) by 534 days.

This patent is subject to a terminal disclaimer.

(21) Appl. No.: 11/678,008

(22) Filed: Feb. 22, 2007

(65) Prior Publication Data

US 2007/0197816 A1 Aug. 23, 2007

Related U.S. Application Data

(60) Provisional application No. 60/775,449, filed on Feb. 22, 2006.

(51) Int. Cl.
C07C 69/96 (2006.01)
(52) U.S. Cl. .................................................. 558/277
(58) Field of Classification Search ................... 558/277
See application file for complete search history.

(56) References Cited

U.S. PATENT DOCUMENTS

| | | | | |
|---|---|---|---|---|
| 2,994,705 | A | 8/1961 | Crosby et al. ............. | 260/340.2 |
| 3,803,201 | A | 4/1974 | Glipin et al. ................. | 260/463 |
| 4,162,200 | A | 7/1979 | Himmele et al. .............. | 203/58 |
| 4,314,945 | A | 2/1982 | McMullen et al. ........ | 260/340.2 |
| 4,434,105 | A | 2/1984 | Buysch et al. .............. | 260/463 |
| 4,508,927 | A | 4/1985 | Bhise et al. .................. | 568/858 |
| 4,691,041 | A | 9/1987 | Duranleeau et al. ......... | 558/277 |
| 5,153,333 | A | 10/1992 | Schubert et al. ............. | 549/230 |
| 5,231,212 | A | 7/1993 | Buysch et al. .............. | 558/277 |
| 5,359,118 | A | 10/1994 | Wagner et al. .............. | 558/277 |
| 5,426,207 | A | 6/1995 | Harrison et al. ............. | 558/274 |
| 5,449,791 | A | 9/1995 | Wagner et al. .............. | 549/230 |
| 5,455,368 | A | 10/1995 | Janisch et al. ................. | 58/277 |
| 5,508,442 | A | 4/1996 | Wagner et al. .............. | 549/228 |
| 5,847,189 | A | 12/1998 | Tojo et al. .................... | 558/277 |
| 6,156,160 | A | 12/2000 | Marquis et al. ............... | 203/29 |
| 6,187,972 | B1 | 2/2001 | Kawabe et al. .............. | 568/858 |
| 6,294,684 | B1 | 9/2001 | de Bruin et al. ............. | 558/274 |
| 6,380,419 | B2 | 4/2002 | Kawabe ....................... | 558/277 |
| 6,392,078 | B1 | 5/2002 | Ryu et al. .................... | 558/277 |
| 6,407,279 | B1 | 6/2002 | Buchanana et al. ......... | 558/227 |
| 6,479,689 | B1 | 11/2002 | Tojo et al. .................... | 558/277 |
| 6,573,396 | B2 | 6/2003 | Buchanan et al. ........... | 558/277 |
| 6,774,256 | B2 | 8/2004 | Schlosberg et al. .......... | 558/277 |
| 7,563,919 | B2 * | 7/2009 | Van Der Heide et al. .... | 558/277 |
| 2007/0197815 | A1 * | 8/2007 | Van Der Heide et al. .... | 558/277 |
| 2008/0183002 | A1 * | 7/2008 | Nisbet et al. ................. | 558/277 |
| 2008/0200711 | A1 * | 8/2008 | Nisbet et al. ................. | 558/260 |

FOREIGN PATENT DOCUMENTS

| | | |
|---|---|---|
| CN | 1060091 | 4/1992 |
| CN | 1102826 | 5/1995 |
| CN | 1528735 | 10/2003 |
| CN | 1528735 | 9/2004 |
| EP | 0001082 | 3/1979 |
| EP | 0274953 | 7/1988 |
| EP | 0297647 | 1/1989 |
| EP | 0180387 | 5/1990 |
| EP | 0583789 | 2/1994 |
| EP | 0776890 | 1/2001 |
| EP | 1174406 | 1/2002 |
| EP | 0119840 | 9/2004 |
| JP | 55-64550 | 5/1980 |
| JP | 61-291545 | 12/1986 |
| JP | 2-212456 | 8/1990 |
| JP | 9-183744 | 7/1997 |
| JP | 2000-005503 | 1/2000 |
| JP | 2003-81893 | 3/2003 |
| JP | 2000-113144 | 4/2003 |
| JP | 2003-155264 | 5/2003 |
| JP | 2003300918 | * 10/2003 |
| JP | 2003-342236 | 12/2003 |
| WO | WO9957108 | 11/1999 |
| WO | WO 0251798 | * 4/2002 |

(Continued)

*Primary Examiner*—James O Wilson
*Assistant Examiner*—Ebenezer Sackey

(57) ABSTRACT

An alkylene carbonate and an alkanol are subjected to transesterification to yield a dialkyl carbonate and alkanediol in a process comprising (a) introducing the alkylene carbonate and an alkanol feedstock into a reaction zone to react in the presence of a transesterification catalyst to yield an alkanediol-rich stream and a stream comprising dialkyl carbonate and alkanol, which streams are separated;

(b) passing the stream comprising dialkyl carbonate and alkanol to an extractive distillation zone in which an extractant is added to the stream;

(c) obtaining from the extractive distillation zone an alkanol-rich vapor stream and a bottom stream containing the extractant and the dialkyl carbonate;

(d) separating the bottom stream from step (c) in a second non-extractive distillation zone to yield a dialkyl carbonate-rich top stream and a extractant-rich bottom stream; and (e) at least partly recycling the extractant-rich bottom stream to the extractive distillation zone, wherein the extractant-rich bottom stream is used as heat source for the alkanol feedstock.

10 Claims, 1 Drawing Sheet

FOREIGN PATENT DOCUMENTS

| WO | WO03006418 | 1/2003 |
| WO | WO03082797 | 10/2003 |
| WO | WO2004056793 | 7/2004 |
| WO | WO2005003113 | 1/2005 |
| WO | WO2005051939 | 6/2005 |

* cited by examiner

PROCESS FOR THE PRODUCTION OF DIALKYL CARBONATE AND ALKANEDIOL

This application claims the benefit of U.S. Provisional Application No. 60/775,449 filed Feb. 22, 2006.

FIELD OF THE INVENTION

The present invention relates to a process for the production of dialkyl carbonate and alkanediol from the reaction between an alkanol and alkylene carbonate.

BACKGROUND

Such a process is known from Chinese patent application CN-A 1528735. This document describes a process in which carbon dioxide is reacted with an alkylene oxide to yield alkylene carbonate, e.g. propylene carbonate or ethylene carbonate. The alkylene carbonate is subjected to transesterification using an alkanol, e.g. methanol, in a reactive distillation column. In this reactive distillation column the alkylene carbonate is fed at the upper part in the liquid phase and the alkanol is fed into the column at a lower part, such that the alkanol flows upward and reacts countercurrently with the alkylene carbonate to obtain dialkyl carbonate with unreacted alkanol as the top effluent and the alkanediol with any entrained alkanol as the bottom effluent. The entrained alkanol is recycled to the reactive distillation column via a reboiler. These products from the top stream are separated in an extractive distillation unit. The extractant used in the process of CN-A 1528735 is the alkylene carbonate.

The document indicates that the energy balance in the known process is not ideal. It suggests a number of improvements. It suggests the generation of low-pressure steam from the exothermic formation of the alkylene carbonate which steam is to be used elsewhere in the process. Another suggestion is to compress part of the top stream of the extractive distillation to provide heat for the reboiler of the reactive distillation column. Although these suggestions may benefit the heat balance of the process, there is room for improvement.

SUMMARY OF THE INVENTION

The present invention provides a process for the production of dialkyl carbonate and alkanediol from the transesterification of alkylene carbonate and alkanol, in which process
(a) the alkylene carbonate and an alkanol feedstock are introduced into a reaction zone to react in the presence of a transesterification catalyst to yield an alkanediol-rich stream and a stream comprising dialkyl carbonate and alkanol which streams are separated;
(b) the stream comprising dialkyl carbonate and alkanol is passed to an extractive distillation zone in which an extractant is added to the stream;
(c) from the extractive distillation zone an alkanol-rich vapor stream is obtained and a bottom stream containing the extractant and the dialkyl carbonate;
(d) the bottom stream from step (c) is separated in a second non-extractive distillation zone to yield a dialkyl carbonate-rich top stream and a extractant-rich bottom stream; and
(e) the extractant-rich bottom stream is at least partly recycled to the extractive distillation zone, wherein the extractant-rich bottom stream is used as a heat source for the alkanol feedstock.

BRIEF DESCRIPTION OF THE DRAWING

The FIGURE shows a flow scheme of an embodiment of the invention.

DETAILED DESCRIPTION

Figure 1:
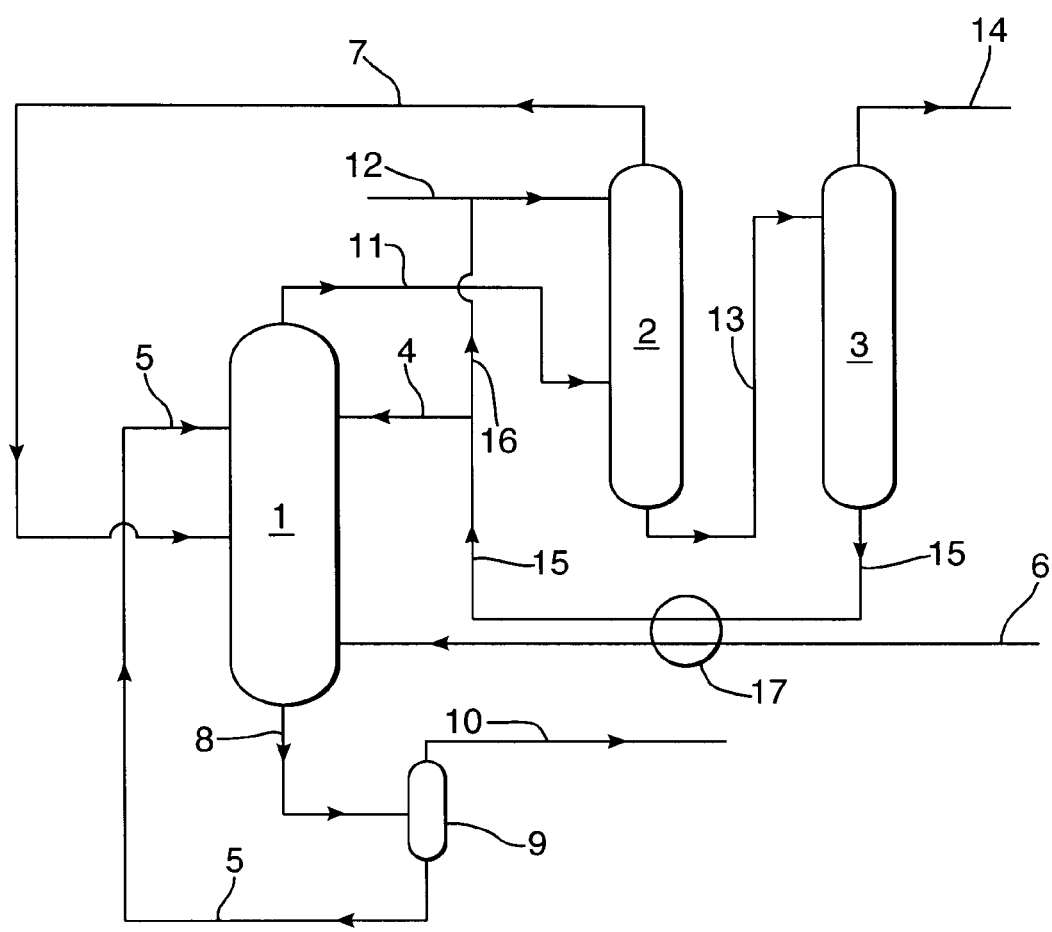

An advantage of the present invention is that the energy that is fed into the extractive distillation can be used elsewhere in the process. A further advantage is that, whereas the prior art suggests the indirect heat exchange by first creating a low pressure steam which can be used as heat source, the present invention allows for direct heat exchange between the extractant-rich bottom stream and the alkanol feedstock. Such a manner would avoid the intermediate step of low-pressure steam creation.

The prior art document referred to above is directed to the preparation of dimethyl carbonate and propylene glycol (1,2-propane diol) from methanol and propylene carbonate. In the extractive distillation propylene carbonate is employed. It is emphasized that the present process is not limited to these specific reactants. The process of the present invention includes the transesterification of an alkylene carbonate with an alkanol. This transesterification reaction is known, as is apparent from e.g. U.S. Pat. No. 5,359,118. The starting materials of the transesterification are preferably selected from $C_2$-$C_6$ alkylene carbonates and $C_1$-$C_4$ alkanols. More preferably the starting materials are ethylene carbonate or propylene carbonate and methanol, ethanol or isopropanol. The most preferred alkanols are methanol and ethanol.

The prior art document also refers to a reactive distillation zone as the reaction zone. It is evident to the skilled person that the reaction can be conducted in other reactors, too. Suitable other reactors include a continuously stirred tank reactor, a plug flow reactor, a trickle flow reactor in either co-current or counter-current mode. However, suitably the reaction is carried out in a reactive distillation zone. Then step a) is operated such that the alkylene carbonate is introduced into the upper part of a reactive distillation zone and an alkanol feedstock is introduced at a lower part of the reactive distillation zone to react in the presence of a transesterification catalyst to yield an alkanediol-rich stream at the bottom and a top stream comprising dialkyl carbonate and alkanol.

The transesterification step is advantageously carried out in a reactive distillation zone into which the alkylene carbonate is fed at the upper part, such that the alkylene carbonate flows down in counter current contact with upwardly moving alkanol. The product of the reaction is a dialkyl carbonate and an alkanediol. The dialkyl carbonate is recovered at the upper part of the zone as the top stream. The alkanediol is recovered as the bottom stream.

The transesterification is suitably conducted in the presence of a catalyst. Suitable catalysts have been described in CN-A 1528735 and U.S. Pat. No. 5,359,118, and include hydrides, oxides, hydroxides, alcoholates, amides, or salts of alkali metals, i.e., lithium, sodium, potassium, rubidium and caesium. Preferred catalysts are hydroxides or alcoholates of potassium or sodium. It is advantageous to use the alcoholate of the alkanol that is being used as feedstock. Such alcoholate can be added as such or being formed in situ.

Other suitable catalysts are alkali metal salts, such as acetates, propionates, butyrates, or carbonates. Further suitable catalysts are described in U.S. Pat. No. 5,359,118 and the references mentioned therein, such as EP-A 274 953, U.S. Pat. No. 3,803,201, EP-A 1082, and EP-A 180 387.

The transesterification conditions are known in the art and suitably include a temperature from 40 to 200° C., and a pressure from 50 to 400 kPa. Preferably, the pressure is close to atmospheric. The temperature depends on the alkanol feedstock and pressure used. The temperature is kept such that it is close to but above the boiling point of the alkanol, suitably up to 5° C. above the boiling point. In the case of methanol and atmospheric pressure, the temperature is close to but above 65° C., e.g., from 65 to 70° C.

The stream comprising dialkyl carbonate and alkanol is subsequently separated into the alkanol-rich stream and the dialkyl carbonate. This is done by extractive distillation since, as indicated in U.S. Pat. No. 5,359,118 and CN-A 1528735. Many alkanols and their corresponding dialkyl carbonates form azeotropes. Therefore it is desirable to use an extractant to facilitate the separation between the dialkyl carbonate and the alkanol. The extractant can be selected from many compounds, in particular alcohols such as phenol, or anisole. Other suitable extractants include aromatic hydrocarbon compounds such as xylene, in particular o-xylene (cf. CN-A 1060091) and dialkyl oxalates, in particular diethyl oxalates (cf. U.S. Pat. No. 6,392,078). However, it is preferred to employ an alkylene carbonate as extractant. It is most advantageous to obtain the separation in the presence of the alkylene carbonate that is being used as starting material for the eventual alkanediol. The most preferred alkenyl carbonate is propenyl carbonate.

The extractive distillation is preferably conducted in two zones. In the first column separation is achieved between the alkanol and a dialkyl carbonate/extractant mixture. In the second zone the separation between the dialkyl carbonate and the extractant is achieved. The extractant is then at least partly recycled to the first zone for renewed use. The ratios between extractant and alkanol and extractant and dialkyl carbonate can be varied between wide ranges. Suitable ranges include from 0.2 to 2.0 moles of extractant per mole of the sum of alkanol and dialkyl carbonate, preferably from 0.4 to 1.0 mole per mole.

When the extractant is an alkylene carbonate it may be advantageous to split the extractant recovered at the second non-extractive distillation zone into a portion that is recycled to the extractive distillation zone and a second portion that is passed to the reactive distillation zone for conversion with the alkanol feedstock. The ratio between alkylene carbonate and alkanol/dialkyl carbonate must in this case be such that the amount of alkylene carbonate is sufficient to allow a good conversion of the portion that is being fed into the reactive distillation zone and an effective separation in the extractive and non-extractive distillation zones.

The distillation conditions for this separation can be selected within wide ranges, as the skilled person will realize. Pressures may suitably range from 5 to 400 kPa, and temperatures from 40 to 200° C. If an alkylene carbonate is used as extractant one has to bear in mind that in view of the stability of the alkylene carbonate the temperature is advantageously not more than 180° C. The lower temperature limit is determined by the boiling point of the alkanol. It is preferred to conduct the separation between alkanol and dialkyl carbonate/extractant mixture at a higher pressure, such as 60 to 120 kPa, and the second separation between dialkyl carbonate and extractant at lower pressure, such as 5 to 50 kPa. This will allow a sufficiently low temperature to retain a satisfactory stability for the alkylene carbonate if such a compound is used as extractant, and an efficient separation between the carbonate compounds. The dialkyl carbonate obtained is recovered as product, optionally after further purification. This further purification may comprise a further distillation step or an ion-exchange step, as described in U.S. Pat. No. 5,455,368.

The hot extractant-rich bottom stream provides a heat source for the alkanol feedstock. Thereto, it is possible to create steam from the bottom stream and use the steam thus created as a source for heating the alkanol feedstock. However, as indicated above, it is advantageous to heat the alkanol feedstock by the extractant-rich bottom stream via heat exchange. This will save additional equipment. The alkanol feedstock is preferably heated to a temperature of 65 to 100° C. Since the alkanol feedstock is suitably fed into the reactive distillation zone in at least a partly vaporous phase, the alkanol feedstock is preferably heated to at least partial vaporization.

As indicated above, the extractant-rich bottom stream leaving the second non-extractive distillation zone preferably has a temperature of not more than 180° C. Its temperature ranges advantageously from 150 to 180° C. Via heat exchange with the alkanol the extractant-rich bottom stream is cooled. Preferably, the stream is cooled to a temperature from 120 to 80° C. by the heat exchange with the alkanol. This will allow a satisfactory heating of the alkanol and the extractant-rich stream remains sufficiently warm to facilitate the first stage of the extractive distillation.

In the FIGURE a reactive distillation zone 1, an extractive distillation zone 2 and a non-extractive distillation zone 3 are shown. The process will now be explained by using propylene carbonate and methanol as examples. It is understood that a person skilled in the art can replace these examples with any other suitable alkylene carbonate and alkanol. Via a line 4 propylene carbonate is fed into the upper part of the reactive distillation zone 1. Via a line 5 a transesterification catalyst is also passed into the upper part of zone 1. Methanol, fed into a lower part of zone 1 via lines 6 and 7, passes upward, and, promoted by the transesterification catalyst, reacts with the propylene carbonate to form propylene glycol product and dimethyl carbonate. The propylene diol is recovered from the bottom of the distillation zone 1 via a line 8. The bottom product in line 8 also contains the catalyst. Therefore the product is separated into a catalyst-containing fraction and a product fraction in a separation unit 9. The separation may be accomplished by distillation. The catalyst is recycled to the zone 1 via line 5, and the propylene glycol is recovered, optionally after further purification (not shown) via a line 10.

It is suitable to use a stoichiometric excess of methanol. Therefore, a mixture of methanol and dimethyl carbonate is passed from the top of the zone 1 via a line 11, and passed to the first extractive distillation zone 2. Via a line 12 propylene carbonate is passed into the extractive distillation zone 2. The extractant, i.e. propylene carbonate, is fed into the extractive zone at a higher level than the mixture of methanol and dimethyl carbonate. The extractive distillation results in the separation of a methanol-rich product, that is passed from the top of the zone 2 via line 7, and that is recycled to the reactive distillation zone 1 as recycle methanol. It is advantageous to feed the recycle methanol at a higher level into the reactive zone 1 than the (make up) methanol that is supplied via line 6.

From the bottom of the extractive distillation a mixture of mainly dimethyl carbonate and propylene carbonate is obtained. This mixture is passed to the second non-extractive distillation zone 3 via line 13. In this distillation the dimethyl carbonate is recovered via line 14 at the top, whereas the propylene carbonate is recovered at the bottom. Via a line 15 the propylene carbonate is split into a stream that via line 4 is fed into the reactive distillation zone 1, and a second stream that via lines 16 and 12 is recycled to the extractive distillation zone 2.

Since the temperature of the propylene carbonate in line 15 is sufficiently high, the methanol that is being supplied to zone 1 via line 6 is subjected to heat exchange in unit 17 with the propylene carbonate in line 15.

It is observed that the flow scheme in the FIGURE is schematic. Other more detailed units, such as refluxes and reboilers in the distillation zones have not been shown. It will also be evident that the products streams in lines 14 and 10 may be further purified.

The invention claimed is:

1. A process for the production of dialkyl carbonate and alkanediol from the transesterification of alkylene carbonate and alkanol, comprising:
   (a) introducing an alkylene carbonate and an alkanol feedstock into a reaction zone to react in the presence of a transesterification catalyst to yield an alkanediol-rich stream and a stream comprising dialkyl carbonate and alkanol which streams are separated;
   (b) passing the stream comprising dialkyl carbonate and alkanol to an extractive distillation zone in which an extractant is added to the stream;
   (c) obtaining from the extractive distillation zone an alkanol-rich vapor stream and a bottom stream containing the extractant and the dialkyl carbonate;
   (d) separating the bottom stream from step (c) in a second non-extractive distillation zone to yield a dialkyl carbonate-rich top stream and a extractant-rich bottom stream; and
   (e) at least partly recycling the extractant-rich bottom stream to the extractive distillation zone, wherein the extractant-rich bottom stream is used as a heat source for the alkanol feedstock.

2. A process according to claim 1, in which in step (a) the alkylene carbonate is introduced into the upper part of a reactive distillation zone and an alkanol feedstock is introduced at a lower part of the reactive distillation zone to react in the presence of a transesterification catalyst to yield an alkanediol-rich stream at the bottom and a top stream comprising dialkyl carbonate and alkanol.

3. A process according to claim 1, in which the extractant is selected from the group consisting of phenol, anisole and alkylene carbonate.

4. A process according to claim 3, in which the alkylene carbonate is propylene carbonate.

5. A process according to claim 1, in which the alkanol is heated by the extractant-rich bottom stream by heat exchange.

6. A process according to claim 5, in which the alkanol is heated to a temperature from 65 to 100° C.

7. A process according to claim 5, in which the alkanol is heated to at least partial vaporization.

8. A process according to claim 1, in which the extractant-rich bottom stream leaves the second non-extractive distillation zone at a temperature of from 150 to 180° C.

9. A process according to claim 1, in which the extractant-rich bottom stream is cooled by heat exchange with the alkanol to a temperature of from 120 to 80° C.

10. A process according to claim 1, in which the pressure in the extractive distillation zone ranges from 60 to 120 kPa, and the pressure in the second non-extractive distillation zone ranges from 5 to 50 kPa.

* * * * *